United States Patent [19]

Kumazawa et al.

[11] Patent Number: 5,189,198
[45] Date of Patent: Feb. 23, 1993

[54] PROCESS FOR PREPARING UNSATURATED DICARBOXYLIC ACID DIESTERS

[75] Inventors: Takashi Kumazawa; Tetsuo Ishibashi; Mitsugu Kanzawa, all of Sodegaura, Japan

[73] Assignee: Idemitsu Petrochemical Co., Ltd., Tokyo, Japan

[21] Appl. No.: 696,053

[22] Filed: May 6, 1991

[30] Foreign Application Priority Data

| | | |
|---|---|---|
| May 17, 1990 [JP] | Japan | 2-125568 |
| Jul. 11, 1990 [JP] | Japan | 2-181648 |
| Oct. 11, 1990 [JP] | Japan | 2-270373 |
| Oct. 12, 1990 [JP] | Japan | 2-272401 |
| Feb. 7, 1991 [JP] | Japan | 3-036566 |

[51] Int. Cl.$^5$ .............................................. C07C 67/38
[52] U.S. Cl. ........................................ 560/81; 560/97; 560/193; 560/204
[58] Field of Search ................. 560/204, 81, 97, 190, 560/193

[56] References Cited

U.S. PATENT DOCUMENTS

| | | | |
|---|---|---|---|
| 3,819,669 | 6/1974 | Knifton | 260/410.9 R |
| 3,892,788 | 7/1975 | Knifton | 260/410.9 R |
| 3,919,272 | 11/1975 | Knifton | 260/410.9 R |

FOREIGN PATENT DOCUMENTS 2844555 4/1980 European Pat. Off. .
2169972 9/1973 France .

OTHER PUBLICATIONS

Patent Abstracts of Japan, C Section, vol. 11, No. 136, Apr. 30, 1987-61-275246.
Patent Abstracts of Japan, C Section, vol. 6, No. 122, Jul. 7, 1982-57-48942.

Primary Examiner—Jose G. Dees
Assistant Examiner—Vera C. Clarke
Attorney, Agent, or Firm—Frishauf, Holtz, Goodman & Woodward

[57] ABSTRACT

A process for efficiently preparing an unsaturated dicarboxylic acid diester, which comprises reacting a conjugated diene, carbon monoxide, an alcohol and oxygen in the presence of a catalyst comprising (a) a platinum metal, a salt thereof or a complex compound of a platinum metal, (b) at least one metal salt selected from the group consisting of a copper salt, an iron salt and a manganese salt and (C) at least one compound selected from the group consisting of (1) an alkali metal compound or an alkaline earth metal compound, (2) a rare earth metal compound, (3) a metal compound of the groups IIIA, IVA, IVB, VA, VB or VIA, and (4) a metal carbonyl complex. The unsaturated dicarboxylic acid diester is useful as an intermediate material in industrial chemical processes and can be efficiently prepared without the use of a dehydrating agent.

19 Claims, No Drawings

PROCESS FOR PREPARING UNSATURATED DICARBOXYLIC ACID DIESTERS

BACKGROUND OF THE INVENTION

1. Field of the Invention

The present invention relates to a process for preparing an unsaturated dicaroboxylic acid diester, and particularly it relates to a process for preparing efficiently an unsaturated dicarboxylic acid diester from a conjugated diene by use of a specific catalyst.

2. Description of Related Arts

Generally, an unsaturated dicarboxylic acid diester such as 2-butene-1,4-dicarboxylic acid diester or the like is important as an intermediate material of a variety of chemical products such as a precusor of adipic acid or the like.

A method for carbonylating a conjugated diene in the presence of an alcohol, carbon monoxide and oxygen is hitherto known, and in order to increase the produced amount of an unsaturated dicarboxylic acid diester a reaction has been carried out substantially in an anhydrous state by the use of a dehydrating agent. However, the conventional methods with use of a dehydrating agent have the following problems (1) - (3) unsolved and needed to be improved.

That is, (1) though an organic compound is used as the dehydrating agent, it becomes a quite different compound after the reaction and is difficult to be reused as a dehydrating agent; (2) the reaction becomes complicated due to by-products derived from the dehydrating agent and the selectivity to carbonylation is decreased; and (3) the operation for realizing an anhydrous state in the reaction system or for the separation after the reaction is complicated.

Thus, the conventional method with use of a dehydrating agent is not suitable for practical use in industry. There has also been proposed a method of adding an aliphatic or alicyclic primary or secondary amine as a method for obtaining the abovementioned objective product (Japanese Patent Application Laid-Open No. 48942/1982). However, this method was also insufficient as a method for industrially preparing an unsaturated dicarboxylic acid diester.

As described above it is the state of things that no industrially effective method has hitherto been known for producing an unsaturated dicarboxylic acid diester such as 2butene-1,4-dicarboxylic acid diester or the like without any dehydrating agent.

The present inventors have earnestly conducted research for the purpose of solving the aforementioned problems in the conventional methods and developing a method for efficiently producing an unsaturated dicarboxylic acid diester from an conjugated diene.

As a result thereof, it has been found that the purpose can be accomplished by the use of a catalyst comprising (a) a platinum metal, a salt thereof or a complex compound of a platinum metal, (b) a salt of a metal selected from copper, iron and manganese and (c) an alkali metal compound, an alkaline earth metal compound, rare earth metal compound, a metal compound of the groups IIIA, IVA, IVB, VA, VB or VIA or a metal carbonyl complex. The present invention has thus been completed based on the knowledge.

SUMMARY OF THE INVENTION

The present invention is to provide a process for preparing an unsaturated dicarboxylic acid diester, which comprises reacting a conjugated diene, carbon monoxide, an alcohol and oxygen in the presence of a catalyst comprising (a) a platinum metal, a salt thereof or a complex compound of a platinum metal, (b) at least one salt of metal selected from copper, iron and manganese and (c) at least one compound selected from (1) an alkali metal compound or an alkaline earth metal compound, (2) a rare earth metal compound, (3) a metal compound of the groups IIIA, IVA, IVB, VA, VB or VIA, and (4) a metal carbonyl complex.

DESCRIPTION OF PREFERRED EMBODIMENTS

The conjugated diene used in the present invention includes a variety of conjugated dienes, from which an appropriate one may be selected depending on the aimed products, and there are generally mentioned the conjugated dienes represented by the general formula (I)

$$R^1HC=C-C=CHR^2 \atop \phantom{R^1HC=}R^3\phantom{-}R^4 \qquad (I)$$

wherein each of $R^1$, $R^2$, $R^3$ and $R^4$ represents hydrogen, halogen, an alkyl group having 1-4 carbon atoms or an aryl group having 6 ring carbons. Specifically, there are mentioned 1,3-butadiene; isoprene; 1,3-pentadiene; 1,3-hexadiene; 2,4-hexadiene; 2,3-dimethylbutadiene; 2,3-diethylbutadiene; 1,4-diphenylbutadiene; chloroprene; 1,3-heptadiene; 2,4-heptadiene; 2-ethyl-1,3-butadiene; 1-phenylbutadiene; 2-chloro-3-methylbutadiene; 1-chlorobutadiene and the like. These conjugated dienes may contain alkanes or alkenes which do not inhibit the reaction.

There can be also used a variety of alcohols which are brought into contact with the aforementioned conjugated diene, and they may be appropriately selected depending on the aimed products and the conjugated dienes as the raw materials. There are generally mentioned monovalent primary, secondary or tertiary alcohols represented by the general formula (II)

$$R^5OH \qquad (II)$$

wherein $R^5$ represents an alkyl group having 1-20 carbon atoms or a cycloalkyl group having 3-20 carbon atoms, preferably an alkyl group having 1-6 carbon atoms. Specifically, there are mentioned methanol, ethanol, n-propanol, isopropanol, n-butanol, cyclohexanol and the like, particularly preferably primary alcohols such as methanol, ethanol, n-propanol, n-butanol and the like.

On the other hand, the catalyst used in the process of the present invention comprises the components (a), (b) and (c). In this connection, the platinum metal as the component (a) includes Pd, Pt, Rh, Ru, Ir and Os, and the salt thereof includes a halide, nitrate, sulfate, acetate, phosphate of these metals. Among these salts, chlorides or acetates of palladium, rhodium or ruthenium are suitably used. The complex of a platinum metal includes an ammine complex, nitrile complex, amine complex, phosphine complex, phosphite complex, arsine complex, stibine complex of a platinum metal or the like. The nitrile includes acetonitrile, benzonitrile or the like. The ligand of the amine, phosphine, phosphite, arsine, stibine or the like is an alkyl group having 1-8 carbon atoms, an aryl, alkylaryl or arylalkyl group having 6-12 carbon atoms, which may be unsubstituted or substituted.

For example, the amine includes monoalkylamines such as methylamine and butylamine; dialkylamines such as dimethylamine and dibutylamine; trialkylamines such as trimethylamine and tributylamine; monoarylamines such as phenylamine; substituted diarylamines such as diphenylamine; substituted triarylamines such as triphenylamine; alkylarylamines such as methylphenylamine.

The phosphine includes methylphosphine, butylphosphine, dibutylphosphine, tributylphosphine, phenylphosphine, diphenylphosphine, triphenylphosphine and the like. The complex includes the complexes having a monodentate ligand or a multidentate ligand. The specific examples of the platinum metal complex include dichlorotetraamminepalladium, dichlorodiamminepalladium, dichlorobisbenzonitrilepalladium, dichlorobisacetonitrilepalladium and the like.

The component (b) is a salt of at least a metal selected from copper, iron and manganese, which includes chlorides, nitrates, sulfates, acetates and the like. As the preferable salts, there are mentioned cuprous chloride, cupric chloride, ferrous chloride, ferric chloride, manganese chloride and the like. These chlorides may be anhydrous or hydrated.

Further, the component (c) can be classified into (1) an alkali metal compound or an alkaline earth metal compound, (2) a rare earth metal compound, (3) a metal compound of the groups IIIA, IVA, IVB, VA, VB or VIA, and (4) a metal carbonyl complex, and various kinds of the compounds can be used and may be appropriately selected depending on aimed products or the conjugated dienes as the raw materials.

First of all, there are mentioned many kinds of compounds for (1) an alkali metal compound or an alkaline earth metal compound. For example, the alkali compound includes carbonates, acetates, chlorides, nitrates, sulfates, phosphates, oxalates, oxides, hydroxides, silicates of Li, Na, K, Rb, Cs and the like, and the alkaline earth metal compound includes carbonates, acetates, chlorides, nitrates, sulfates, oxides of Mg, Ca, Sr, Ba and the like. Among these compounds, the carbonates and acetates of the alkaline earth metals are particularly effective. Further, it is also possible to use the alkali metal salt or the alkaline earth metal salt of a monocarboxylic acid represented by the general formula (III)

$$R^6COOM \qquad (III)$$

wherein $R^6$ represents an alkyl group having 2-10 carbon atoms or a cycloalkyl group having 3-10 carbon atoms, and M represents an alkali metal or an alkaline earth metal, or the alkali metal salt or the alkaline earth metal salt of a dicarboxylic acid represented by the general formula (IV)

$$MOOCR^7COOM \qquad (IV)$$

wherein $R^7$ represents an alkyl group having 1-10 carbon atoms or a cycloalkyl group having 3-10 carbon atoms, and M represents an alkali metal or an alkaline earth metal. For example, the monocarboxylic acid includes propionic acid, butyric acid, valeric acid, capronic acid and the like, and the dicarboxylic acid includes malonic acid, succinic acid, glutaric acid, adipic acid, suberic acid, sebacic acid and the like. As the alkali metal salts of these carboxylic acids, there are mentioned sodium salts, potassium salts, lithium salts, rubidium salts, cesium salts and the like, and as the alkaline earth metal salts there are mentioned magnesium salts, calcium salts, strontium salts, barium salts and the like. Among these compounds, the alkali metal salts of the dicarboxylic acids are preferred.

Next, there are mentioned many kinds of compounds for (2) the rare earth metal compounds. For example, there are mentioned metals such as Sc, Y, La, Ce, Pr, Nd, Pm, Sm, Eu, Gd, Tb, Dy, Ho, Er, Tm, Yb, Lu and the like. As the compounds of these metals, there are mentioned carbonates, chlorides, nitrates, sulfates, oxides, acetates, organic acid salts and the like. Among these compounds, there are preferably mentioned lanthanum compounds such as lanthanum carbonate, lanthanum oxide and lanthanum acetate; cerium compounds such as cerium carbonate and cerium oxide; yttrium compounds such as yttrium carbonate and yttrium oxide; neodymium compounds such as neodymium carbonate and neodymium oxide; ytterbium compounds such as ytterbium carbonate and ytterbium oxide; holmium compounds such as holmium carbonate and holmium oxide; and samarium compounds such as samarium carbonate and samarium oxide.

Also, there are mentioned many kinds of compounds for (3) the compounds of the metals belonging to the group IIIA, IVA, IVB, VA, VB or VIA of the periodic table. For example, there are mentioned carbonates, chlorides, nitrates, sulfates, oxides, acetates and organic acid salts of Al, Ga, In, Tl, Ge, Sn, Pb, Ti, Zr, Hf, Sb, Bi, Nb, Ta, Te and the like. Among these compounds there are preferably mentioned the oxides and carbonates of bismuth, lead, indium and the like.

Further, as the metal carbonyl complex (4), there are usually used carbonyl compounds of metals in the groups IVB, VB, VIB, VIIB and VIII. Among these compounds, there are preferably employed particularly $Fe(CO)_5$, $Co_2(CO)_8$, $Mn_2(CO)_{10}$, $Cr(CO)_6$, $Mo(CO)_8$, $W(CO)_8$, $V(CO)_8$, $Ru(CO)_5$, $Rh_4(CO)_{12}$ and $Os(CO)_5$.

As for the component (c), one or more of the compounds (1)-(4) may be used.

Although the amount of the catalyst used in the present invention is not specifically limited, the component (a) is used in an amount of 0.01-50 g atoms, preferably 0.05-20 g atoms as the metal per 100 moles of the conjugated diene as a raw material. Also, the component (b) is used generally in an amount of 0.1-100 moles, preferably 0.5-50 moles per 1 g atom of the platinum metal or 1 mole of the salt or the complex of the platinum metal of the component (a). Further, the component (c) is generally used in an amount of 0.1-100 moles preferably 0.5-50 moles per 1 g atom of the platinum metal or 1 mole of the salt or the complex of the platinum metal of the component (a).

In this connection, the components (a), (b) and (c) may be carried on active carbon, silica, alumina, silica-alumina, zeolite, clay or the like, or they may be fixed on a polymer carrier.

The reaction in the present invention can be carried out in the absence or presence of a solvent which will not interfere with the reaction. Typical solvents which will not interfere with the reaction include ethers such as 1,4-dioxane, tetrahydrofuran and diethyl ether; chlorinated compounds such as dichloromethane, carbon tetrachloride, trichloroethane and 1,2-dichloroethane; esters such as methyl acetate, ethyl acetate and dimethyl adipate; ketones such as methyl ethyl ketone and methyl isobutyl ketone; aromatic hydrocarbons such as benzene and toluene; alicyclic hydrocarbons such as cyclohexane and methylcyclohexane; nitriles such as acetonitrile; sulfolan.

The reaction temperature is generally in the range of 30°–200° C., preferably in the range of 60°–150° C. If the temperature is excessively high, selectivity is often decreased. At low temperature, the reaction rate is lowered to an unpractical level. The reaction pressure may be in the range so that the partial pressure of carbon monoxide is in the range of 20–600 kg/cm$^2$G as a measure. At an excessively low pressure, the reaction rate is lowered, while at an excessively high pressure a reaction apparatus having a large size is required and thus an expensively high cost is required disadvantageously in economy for constructing the apparatus.

The reaction in the present invention proceeds in the presence of oxygen, which is sufficient to be an oxygen containing gas such as pure oxygen or air. In this connection, the partial pressure of oxygen is desirably adjusted to ensure that the mixed gas in the reaction apparatus has a composition out of the explosion range.

The reaction can be carried out in either batchwise, semi-continuous or continuous mode. The reaction system may be in the state of a liquid phase or a gas phase or in the mixed state of a liquid phase and a gas phase. The catalyst may be either homogeneous or heterogeneous in the reaction system, and a solvent and a catalyst may be selected appropriately.

The process of the present invention is to prepare an unsaturated dicarboxylic acid diester by the reaction of the above-described conjugated diene, an alcohol and carbon monoxide (CO). When the compound represented by the general formula (I) as the conjugated diene and the compound represented by the general formula (II) as the alcohol are employed for raw materials, there can be produced an unsaturated dicarboxylic acid diester represented by the general formula (V)

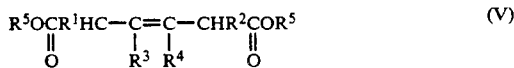
(V)

wherein R$^1$–R$^5$ have the same meanings defined above.

When 1,3-butadiene is employed as the conjugated diene, the reaction represented by the following equation proceeds

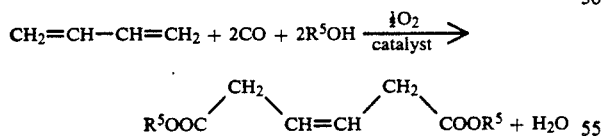

wherein R$_1$–R$^5$ have the same meanings as defined above.

As the unsaturated dicarboxylic acid diester which is the product obtained by the reaction, there are mentioned various diesters such as dimethyl 2-butene-1,4-dicarboxylate, diethyl 2-butene-1,4-dicarboxylate, dimethyl 1-methyl-2-butene-1,4-dicarboxylate, diethyl 1-methyl-2-dicarboxylate, dimethyl 1,1,4,4-tetramethyl-2-butene-1,4-dicarboxylate, diethyl 1,1,4,4-tetramethyl-2-butene-1,4-dicarboxylate, dimethyl 1,4-diphenyl-2-butene-1,4-dicarboxylate, diethyl 1,4-diphenyl-2-butene-1,4-dicarboxylate, and the like.

According to the process of the present invention, an unsaturated dicarboxylic acid diester which will be a useful intermediate in chemical industry can be produced in a high yield with use of the aforementioned catalyst and without use of a dehydrating agent.

Therefore, the present invention is expected to be applied effectively in the field of chemical industry as a process for producing efficiently an unsaturated dicarboxylic acid diester as a raw material of the intermediate of a variety of chemical products The present invention is now described more specifically with reference to examples and comparative examples The present invention, however, is not limited to these examples.

In the following examples, the component (c) of the present invention is (1) an alkali metal compound or an alkaline earth metal compound in Example A, an alkali metal salt or an alkaline earth metal salt of a monocarboxylate or a dicarboxylate in Example B, (2) a rare earth compound in Example C, (3) a metal compound of the group IIIA, IVA, IVB, VA, VB or VIA in Example D, and (4) a carbonyl complex in Example E.

EXAMPLE A-1

To an autoclave having an internal volume of 200 ml and equipped with a stirrer, there were introduced 1 mmol (millimole) of palladium chloride, 2.3 mmol of cupric chloride, 16 ml of methanol, 74 ml of dioxane and 2 mmol of strontium carbonate. After the autoclave was sealed tightly, 200 mmol of 1,3-butadiene was charged and 71 kg/cm$^2$G of carbon monoxide and 3.6 kg/cm$^2$G of oxygen were injected with pressure to a total pressure of 74.6 kg/cm$^2$G.

The system was heated to 100° C., and reaction was conducted at a stirring rate of 500 rpm for 3 hours. During the reaction, oxygen was supplied in 3 portions within the range so that an explosive gas mixture would not be formed in the vapor phase of the autoclave. Total amount of oxygen supplied corresponded to 12 kg/cm$^2$G.

Gas chromatographical analysis of the reaction mixture after the reaction revealed that dimethyl 2-butene-1,4-dicarboxylate was produced in a yield of 29.5 mmol.

Example A-2

Reaction was conducted in the same manner as in Example A-1 except that strontium carbonate was replaced with barium carbonate. During the reaction for 3 hours, oxygen was supplied in an amount corresponding to 12 kg/cm$^2$G.

Gas chromatographical analysis of the reaction mixture after the reaction revealed that dimethyl 2-butene-1,4-dicarboxylate was given in a yield of 27.5 mmol.

Example A-3

Reaction was conducted in the same manner as in Example A-1 except that strontium carbonate was replaced with strontium acetate. During the reaction for 3 hours, oxygen was supplied in an amount corresponding to 12 kg/cm$^2$G.

Gas chromatographical analysis of the reaction mixture after the reaction revealed that dimethyl 2-butene-1,4-dicarboxylate was given in a yield of 22.7 mmol.

Example A-4

Reaction was conducted in the same manner as in Example A-1 except that strontium carbonate was replaced with strontium nitrate. During the reaction for 3 hours, oxygen was supplied in an amount corresponding to 13 kg/cm²G.

Gas chromatographical analysis of the reaction mixture after the reaction revealed that dimethyl 2-butene-1,4-dicarboxylate was given in a yield of 18.6 mmol.

Example A-5

Reaction was conducted in the same manner as in Example A-1 except that strontium carbonate was replaced with strontium chloride. During the reaction for 3 hours, oxygen was supplied in an amount corresponding to 12 kg/cm²G.

Gas chromatographical analysis of the reaction mixture after the reaction revealed that dimethyl 2-butene-1,4-dicarboxylate was given in a yield of 7.5 mmol.

Example A-6

Reaction was conducted in the same manner as in Example A-1 except that strontium carbonate was replaced with calcium carbonate. During the reaction for 3 hours, oxygen was an amount corresponding to 12 kg/cm²G. Dimethyl 2-butene-1,4-dicarboxylate was given in a yield of 22.5 mmol.

Example A-7

Reaction was conducted in the same manner as in Example A-1 except that 1 mmol of lithium carbonate was used in place of strontium carbonate. The amount of oxygen supplied was 12 kg/cm²G. Dimethyl 2-butene-1,4-dicarboxylate was given in a yield of 19.7 mmol.

Example A-8

Reaction was conducted in the same manner as in Example A-1 except that cupric chloride was replaced with ferric chloride. The amount of oxygen supplied was 12 kg/cm²G. Dimethyl 2-butene-1,4-dicarboxylate was given in a yield of 21.3 mmol.

Example A-9

To an autoclave having an internal volume of 200 ml and equipped with a stirrer, there were introduced 0.3 mmol of dichlorotetraamminepalladium, 3.3 mmol of cupric chloride, 10 ml of methanol, 80 ml of dioxane and 2 mmol of strontium carbonate. After the autoclave was sealed tightly, 200 mmol of 1,3-butadiene was charged and 71 kg/cm²G of carbon monoxide and 3.6 kg/cm²G of oxygen were injected with pressure to a total pressure of 74.6 kg/cm²G.

The reaction system was heated to 100° C., and reaction was conducted at a stirring rate of 500 rpm for 3 hours. During the reaction, oxygen was supplied in 3 portions within the range so that an explosive gas mixture would not be formed in the vapor phase of the autoclave. Total amount of oxygen supplied corresponded to 12 kg/cm²G.

Gas chromatographical analysis of the reaction mixture after the reaction revealed that dimethyl 2-butene-1,4dicarboxylate was produced in a yield of 26.5 mmol.

Example A-10

Reaction was conducted in the same manner as in Example A-9 except that 1 mmol of barium carbonate was used in place of strontium carbonate. During the reaction for 3 hours, oxygen in an amount of 12 kg/cm²G was supplied.

Gas chromatographical analysis of the reaction mixture after the reaction revealed that dimethyl 2-butene-1,4-dicarboxylate was given in a yield of 22.3 mmol.

Example A-11

Reaction was conducted in the same manner as in Example A-10 except that dichlorotetraamminepalladium was replaced with dichlorodiamminepalladium. During the reaction for 3 hours, oxygen was supplied in an amount of 12 kg/cm²G.

Gas chromatographical analysis of the reaction mixture after the reaction revealed that dimethyl 2-butene-1,4-dicarboxylate was given in a yield of 21.3 mmol.

Example A-12

Reaction was conducted in the same manner as in Example A-10 except that dichlorotetraamminepalladium was replaced with dichlorobisbenzonitrilepalladium. During the reaction for 3 hours, oxygen was supplied in an amount of 12 kg/cm²G.

Gas chromatographical analysis of the reaction mixture after the reaction revealed that dimethyl 2-butene-1,4-dicarboxylate was given in a yield of 19.4 mmol.

Example A-13

Reaction was conducted in the same manner as in Example A-10 except that dichlorotetraamminepalladium was replaced with dichlorobisacetonitrilepalladium. During the reaction for 3 hours, oxygen was supplied in an amount of 12 kg/cm²G.

Gas chromatographical analysis of the reaction mixture after the reaction revealed that dimethyl 2-butene-1,4-dicarboxylate was given in a yield of 21.6 mmol.

Example A-14

Reaction was conducted in the same manner as in Example A-1 except that 0.3 mmol of palladium chloride, 3.0 mmol of cupric chloride, 10 ml of methanol and 80 ml of dioxane were used and strontium carbonate was replaced with 2.0 mmol of strontium oxide.

Dimethyl 2-butene-1,4-dicarboxylate after the reaction was given in a yield of 26.1 mmol.

Example A-15

Reaction was conducted in the same manner as in Example A-14 except that strontium carbonate was replaced with 1.0 mmol of barium oxide.

Dimethyl 2-butene-1,4-dicarboxylate after the reaction was given in a yield of 25.1 mmol.

Example A-16

Reaction was conducted in the same manner as in Example A-1 except that 0.3 mmol of palladium chloride, 3.0 mmol of cupric chloride, 10 ml of methanol and 80 ml of dioxane were used and 1,3-butadiene was replaced with a mixed gas in such an amount as the concentration of 1,3-butadiene is 200 mmol. The mixed gas had a composition comprising 44.2% of 1,3-butadiene, 26.3% of isobutene, 15.3% of cis-2-butene and 14.2% of 1-butene.

Dimethyl 2-butene-1,4-dicarboxylate after the reaction was given in a yield of 22.2 mmol.

Example A-17

Reaction was conducted in the same manner as in Example A-14 except that strontium oxide was replaced with 1.0 mmol of sodium hydroxide.

Dimethyl 2-butene-1,4-dicarboxylate after the reaction was given in a yield of 14.0 mmol.

Example A-18

Reaction was conducted in the same manner as in Example A-14 except that strontium oxide was replaced with 2.0 mmol of sodium acetate.

Dimethyl 2-butene-1,4-dicarboxylate after the reaction was given in a yield of 8.2 mmol.

Example A-19

Reaction was conducted in the same manner as in Example A-1 except that 1,3-butadiene was replaced with 1,3-pentadiene.

Gas chromatographical analysis of the reaction mixture after the reaction revealed that dimethyl 2-pentene-1,3-dicarboxylate was given in a yield of 17.6 mmol and dimethyl 2-pentene-1,5-dicarboxylate in a yield of 3.3 mmol.

Example A-20

Reaction was conducted in the same manner as in Example A-1 except that 1,3-butadiene was replaced with isoprene.

Gas chromatographical analysis of the reaction mixture after the reaction revealed that dimethyl 2-methyl-2-butene-1,4-dicarboxylate was given in a yield of 28.6 mmol.

Comparative Example A-1

Reaction was conducted in the same manner as in Example A-1 except that no strontium carbonate was used. During the reaction for 3 hours, oxygen was supplied in an amount of 13 kg/cm$^2$G. Dimethyl 2-butene-1,4-dicarboxylate was given merely in a yield of 1.5 mmol.

Comparative Example A-2

Reaction was conducted in the same manner as in Example A-1 except that strontium carbonate was replaced with 3.0 mmol of n-butylamine.

Gas chromatographical analysis of the reaction mixture after the reaction revealed that dimethyl 2-butene-1 4-dicarboxylate was given merely in a yield of 4.6 mmol.

Example B-1

To an autoclave having an internal volume of 200 ml and equipped with a stirrer, there were introduced 0.5 mmol of palladium chloride, 5.0 mmol of cupric chloride, 2.0 mmol of disodium adipate, 16 ml of methanol and 74 ml of dioxane. After the autoclave was sealed tightly, 200 mmol of 1,3-butadiene was charged and 75.2 kg/cm$^2$G of carbon monoxide and 3.8 kg/cm$^2$G of oxygen were injected with pressure to a total pressure of 79.0 kg/cm$^2$G. The reaction system was heated to 100° C., and reaction was conducted at a stirring rate of 500 rpm for 3 hours. During the reaction, oxygen was supplied in 3 portions within the range so that an explosive gas mixture would not be formed in the vapor phase of the autoclave. Total amount of oxygen supplied corresponded to 12.3 kg/cm$^2$G.

Gas chromatographical analysis of the reaction mixture after the reaction revealed that dimethyl 2-butene-1,4-dicarboxylate was produced in a yield of 30.0 mmol.

Example B-2

Reaction was conducted in the same manner as in Example B-1 except that disodium adipate was replaced with disodium glutarate.

Gas chromatographical analysis of the reaction mixture after the reaction revealed that dimethyl 2-butene-1,4-dicarboxylate was given in a yield of 26.7 mmol.

Example B-3

Reaction was conducted in the same manner as in Example B-1 except that disodium adipate was replaced with 4.0 mmol of disodium malonate.

Gas chromatographical analysis of the reaction mixture after the reaction revealed that dimethyl 2-butene-1,4-dicarboxylate was given in a yield of 26.6 mmol.

Example B-4

Reaction was conducted in the same manner as in Example B-1 except that disodium adipate was replaced with sodium n-caproate Gas chromatographical analysis of the reaction mixture after the reaction revealed that dimethyl 2-butene-1 4-dicarboxylate was given in a yield of 12.9 mmol.

Example B-5

Reaction was conducted in the same manner as in Example B-1 except that disodium adipate was replaced with sodium butyrate.

Gas chromatographical analysis of the reaction mixture after the reaction revealed that dimethyl 2-butene-1,4dicarboxylate was given in a yield of 10.6 mmol.

Example B-6

Reaction was conducted in the same manner as in Example B-1 except that palladium chloride was replaced with dichlorotetraamminepalladium. During the reaction for 3 hours, oxygen was supplied in an amount of 12 kg/cm$^2$G.

Gas chromatographical analysis of the reaction mixture after the reaction revealed that dimethyl 2-butene-1,4-dicarboxylate was given in a yield of 30.5 mmol.

Comparative Example B-1

Reaction was conducted in the same manner as in Example B-1 that 1.0 mmol of palladium chloride and 2.3 mmol of cupric chloride were used and disodium adipate was not used. During the reaction for 3 hours, oxygen was supplied in an amount of 13 kg/cm$^2$G.

Gas chromatographical analysis of the reaction mixture after the reaction revealed that dimethyl 2-butene-1,4-dicarboxylate was given merely in a yield of 1.5 mmol.

Comparative Example B-2

Reaction was conducted in the same manner as in Example B-1 except that 1.0 mmol of palladium chloride and 2.3 mmol of cupric chloride were used and disodium adipate was replaced with 3.0 mmol of n-butylamine.

Gas chromatographical analysis of the reaction mixture after the reaction revealed that dimethyl 2-butene-1,4-dicarboxylate wa given merely in a yield of 4.6 mmol.

Example C-1

To an autoclave having an internal volume of 200 ml and equipped with a stirrer, there were introduced 0.3 mmol of palladium chloride, 3.0 mmol of cupric chloride, 2.0 mmol of lanthanum carbonate, 10 ml of methanol and 80 ml of dioxane. After the autoclave was sealed tightly, 200 mmol of 1,3-butadiene butadiene was charged and 74.5 kg/cm$^2$G of carbon monoxide and 3.9 kg/cm$^2$G of oxygen were injected with pressure to a total pressure of 78.4 kg/cm$^2$G. The reaction system was heated to 100° C., and reaction was conducted at a stirring rate of 500 rpm for 3 hours. During the reaction, oxygen was supplied in 3 portions within the range so that an explosive gas mixture would not be formed in the vapor phase of the autoclave. Total amount of oxygen supplied corresponded to 12.9 kg/cm$^2$G.

Gas chromatographical analysis of the reaction mixture after the reaction revealed that dimethyl 2-butene-1,4-dicarboxylate was produced in a yield of 30.4 mmol.

Example C-2

Reaction was conducted in the same manner as in Example C-1 except that lanthanum carbonate was replaced with lanthanum oxide.

Gas chromatographical analysis of the reaction mixture after the reaction revealed that dimethyl 2-butene-1,4-dicarboxylate was given in a yield of 26.1 mmol.

Example C-3

.Reaction was conducted in the same manner as in Example C-1 except that lanthanum carbonate was replaced with lanthanum acetate.

Gas chromatographical analysis of the reaction mixture after the reaction revealed that dimethyl 2-butene-1,4-dicarboxylate was given in a yield of 24.8 mmol.

Example C-4

Reaction was conducted in the same manner as in Example C-1 except that lanthanum carbonate was replaced with cerium carbonate.

Gas chromatographical analysis of the reaction mixture after the reaction revealed that dimethyl 2-butene-1,4-dicarboxylate was given in a yield of 25.8 mmol.

Example C-5

Reaction was conducted in the same manner as in Example C-1 except that lanthanum carbonate was replaced with ceric oxide.

Gas chromatographical analysis of the reaction mixture after the reaction revealed that dimethyl 2-butene-1,4dicarboxylate was given in a yield of 26.1 mmol.

Example C-6

Reaction was conducted in the same manner as in Example C-1 except that lanthanum carbonate was replaced with yttrium carbonate.

Gas chromatographical analysis of the reaction mixture after the reaction revealed that dimethyl 2-butene-1,4-dicarboxylate was given in a yield of 25.9 mmol.

Example C-7

Reaction was conducted in the same manner as in Example C-1 except that lanthanum carbonate was replaced with neodymium carbonate.

Gas chromatographical analysis of the reaction mixture after the reaction revealed that dimethyl 2-butene-1,4-dicarboxylate was given in a yield of 25.3 mmol.

Example C-8

Reaction was conducted in the same manner as in Example C-1 except that lanthanum carbonate was replaced with ytterbium carbonate.

Gas chromatographical analysis of the reaction mixture after the reaction revealed that dimethyl 2-butene-1,4-dicarboxylate was given in a yield of 25.4 mmol.

Example C-9

Reaction was conducted in the same manner as in Example C-1 except that palladium chloride was replaced with dichlorotetraamminepalladium. During the reaction for 3 hours, oxygen was supplied in an amount of 13 kg/cm$^2$G.

Gas chromatographical analysis of the reaction mixture after the reaction revealed that dimethyl 2-butene-1,4-dicarboxylate was given in a yield of 29.8 mmol.

Comparative Example C-1

Reaction was conducted in the same manner as in Example C-1 except that 1.0 mmol of palladium chloride and 2.3 mmol of cupric chloride were used and no lanthanum carbonate was used. During the reaction for 3 hours, oxygen was supplied in an amount of 13 kg/cm$^2$G.

Gas chromatographical analysis of the reaction mixture after the reaction revealed that dimethyl 2-butene-1,4-dicarboxylate was given merely in a yield of 1.5 mmol.

Comparative Example C-2

Reaction was conducted in the same manner as in Example C-1 except that 1.0 mmol of palladium chloride and 2.3 mmol of cupric chloride were used and lanthanum carbonate was replaced with 3.0 mmol of n-butylamine.

Gas chromatographical analysis of the reaction mixture after the reaction revealed that dimethyl 2-butene-1,4-dicarboxylate was given merely in a yield of 4.6 mmol.

Example D-1

To an autoclave having an internal volume of 200 ml and equipped with a stirrer, there were introduced 0.3 mmol of palladium chloride, 3.0 mmol of cupric chloride, 2.0 mmol of bismuth oxide, 10 ml of methanol and 80 ml of dioxane. After the autoclave was sealed tightly, 200 mmol of 1,3-butadiene was charged and 72.5 kg/cm$^2$G of carbon monoxide and 3.6 kg/cm$^2$ of oxygen were injected with pressure to a total pressure of 76.1 kg/cm$^2$G. The reaction system was heated to 100° C., and reaction was conducted at a stirring rate of 500 rpm for 3 hours. During the reaction, oxygen was supplied in 3 portions within the range so that an explosive gas mixture would not be formed in the vapor phase of the autoclave. Total amount of oxygen supplied corresponded to 12.2 kg/cmn$^2$G. Gas chromatographical analysis of the reaction mixture after the reaction revealed that dimethyl 2-butene-1,4-dicarboxylate was produced in a yield of 29.1 mmol.

Example D-2

Reaction was conducted in the same manner as in Example D-1 except that bismuth oxide was replaced with lead oxide. After the reaction, dimethyl 2-butene-1,4-dicarboxylate was given in a yield of 27.8 mmol.

Example D-3

Reaction was conducted in the same manner as in Example D-1 except that bismuth oxide was replaced with indium oxide. After the reaction, dimethyl 2-butene-1,4-dicarboxylate was given in a yield of 25.7 mmol.

Example D-4

Reaction was conducted in the same manner as in Example D-1 except that bismuth oxide wa replaced with bismuth carbonate. After the reaction, dimethyl 2-butene-1,4-dicarboxylate was given in a yield of 26.5 mmol.

Example D-5

Reaction was conducted in the same manner as in Example D-1 except that bismuth oxide was replaced with lead carbonate. After the reaction, dimethyl 2-butene-1,4-dicarboxylate was given in a yield of 28.3 mmol.

Example D-6

Reaction was conducted in the same manner as in Example D-1 except that bismuth oxide was replaced with thallium oxide. After the reaction, dimethyl 2-butene-1,4-dicarboxylate was given in a yield of 12.5 mmol.

Example D-7

Reaction was conducted in the same manner as in Example D-1 except that bismuth oxide was replaced with thallium acetate. After the reaction, dimethyl 2-butene-1,4-dicarboxylate was given in a yield of 12.1 mmol.

Example D-8

Reaction was conducted in the same manner as in Example D-1 except that bismuth oxide wa replaced with tantalum oxide. After the reaction, dimethyl 2-butene-1,4-dicarboxylate was given in a yield of 12.6 mmol.

Example D-9

Reaction was conducted in the same manner as in Example D-1 except that bismuth oxide was replaced with niobium oxide. After the reaction, dimethyl 2-butene-1,4-cicarboxylate was given in a yield of 10.6 mmol.

Example D-10

Reaction was conducted in the same manner as in Example D-1 except that bismuth oxide was replaced with tellurium oxide. After the reaction, dimethyl 2-butene-1,4-dicarboxylate was given in a yield of 12.0 mmol.

Example D-11

Reaction was conducted in the same manner as in Example D-1 except that bismuth oxide was replaced with antimony oxide. After the reaction, dimethyl 2-butene-1,4-dicarboxylate was given in a yield of 10.6 mmol.

Example D-12

Reaction was conducted in the same manner as in Example D-1 except that bismuth oxide was replaced with 1.0 mmol of tin oxide. After the reaction, dimethyl 2-butene-1,4-dicarboxylate was given in a yield of 10.0 mmol.

Example D-13

Reaction was conducted in the same manner as in Example D-1 except that bismuth oxide was replaced with hafnium oxide. After the reaction, dimethyl 2-butene-1,4-dicarboxylate was given in a yield of 10.2 mmol.

Example D-14

Reaction was conducted in the same manner as in Example D-1 except that bismuth oxide was replaced with zirconium oxide. After the reaction, dimethyl 2-butene-1,4-dicarboxylate was given in a yield of 10.0 mmol.

Comparative Example D-1

Reaction was conducted in the same manner as in Example D-1 except that 1.0 mmol of palladium chloride and 2.3 mmol of cupric chloride were used and bismuth oxide was not used. After the reaction, dimethyl 2-butene-1,4-dicarboxylate was given merely in a yield of 1.5 mmol.

Comparative Example D-2

Reaction was conducted in the same manner as in Example D-1 except that 1.0 mmol of palladium chloride and 2.3 mmol of cupric chloride were used and bismuth oxide was replaced with 3.0 mmol of n-butylamine. After the reaction, dimethyl 2butene-1,4-dicarboxylate was given merely in a yield of 4.6 mmol.

Example E-1

To an autoclave having an internal volume of 150 ml and equipped with a stirrer, there were introduced 1.0 mmol of palladium chloride, 4.0 mmol of cupric chloride, 400 mmol of methanol, 25 g of dioxane and 4.0 mmol of Co CO)$_8$. After the autoclave was sealed tightly, 200 mmol of 1,3-butadiene was charged and 80.0 kg/cm$^2$G of carbon monoxide and 5.0 kg/cm$^2$G of oxygen were injected with pressure to a total pressure of 85.0 kg/cm$^2$. The reaction system was heated to 100° C., and reaction was conducted at a stirring rate of 500 rpm for 3 hours. During the reaction, oxygen was supplied in 4 portions within the range so that an explosive gas mixture would not be formed in the vapor phase of the autoclave. Total amount of oxygen supplied corresponded to 20 kg/cm$^2$G.

Gas chromatographical analysis of the reaction mixture after the reaction revealed that dimethyl 2-butene-1,4dicarboxylate was produced in a yield of 26.0 mmol.

Example E-2

Reaction was conducted in the same manner as in Example E-1 except that Co$_2$(CO)$_8$ was replaced with Fe(CO)$_5$.

Gas chromatographical analysis of the reaction mixture after the reaction revealed that dimethyl 2-butene-1,4-dicarboxylate was produced in a yield of 24.4 mmol.

Example E-3

Reaction was conducted in the same manner as in Example E-1 except that cupric chloride was replaced with manganese chloride.

Gas chromatographical analysis of the reaction mixture after the reaction revealed that dimethyl 2-butene-1,4-dicarboxylate was produced in a yield of 22.3 mmol.

Example E-4

Reaction was conducted in the same manner as in Example E-1 except that cupric chloride was replaced with 4.0 mmol of ferric chloride.

Gas chromatographical analysis of the reaction mixture after the reaction revealed that dimethyl 2-butene-1,4-dicarboxylate was produced in a yield of 23.5 mmol.

Comparative Example E-1

Reaction was conducted in the same manner as in Example E-1 except that no $Co_2(CO)_8$ was added.

Gas chromatographical analysis of the reaction mixture after the reaction revealed that dimethyl 2-butene-1,4-dicarboxylate was produced merely in a yield of 0.02 mmol.

Comparative Example E-2

Reaction was conducted in the same manner as in Example E-1 except that $Co_2(CO)_8$ was replaced with 4.0 mmol of n-butylamine.

Gas chromatographical analysis of the reaction mixture after the reaction revealed that dimethyl 2-butene-1,4dicarboxylate was produced merely in a yield of 5.0 mmol.

Comparative Example E-3

Reaction was conducted in the same manner as in Comparative Example E-1 except that cupric chloride was replaced with 4.0 mmol of manganese chloride.

Gas chromatographical analysis of the reaction mixture after the reaction revealed that dimethyl 2-butene-1,4-dicarboxylate was produced merely in a yield of 0.01 mmol.

Comparative Example E-4

Reaction was conducted in the same manner as in Comparative Example E-1 except that cupric chloride was replaced with 4.0 mmol of ferric chloride.

Gas chromatographical analysis of the reaction mixture after the reaction revealed that dimethyl 2-butene-1,4-dicarboxylate was produced merely in a yield of 0.01 mmol.

What is claimed is:

1. A process for preparing an unsaturated dicarboxylic acid diester, which comprises reacting a conjugated diene, carbon monoxide, an alcohol and oxygen at a temperature of 30° to 200° C. and at a partial pressure of carbon monoxide of 20 to 600 kg/cm²G in the presence of a catalyst comprising
   (a) 0.01 to 50 g atoms as a metal per 100 moles of said conjugated diene of a platinum metal, a salt thereof or an ammine complex, a nitrile complex, an amine complex, a phosphine complex, a phosphite complex, an arsine complex or a stibine complex compound of said platinum metal,
   (b) 0.1 to 100 moles per 1 g atom of said platinum metal or 1 mole of said salt of said complex of said platinum metal of at least one metal salt selected from the group consisting of a copper salt, an iron salt and a manganese salt and
   (c) 0.1 to 100 moles per 1 g atom of said platinum metal or 1 mole of said salt or said complex of said platinum metal of at least one compound selected from the group consisting of (i) an alkali metal compound or an alkaline earth metal compound, (ii) a rare earth metal compound, (iii) a metal compound of the groups IIIA, IVA, IVB, VA, VB or VIA, and (iv) a metal carbonxyl compound of the groups VIB, VIIB or VIII.

2. The process according to claim 1, wherein said conjugated diene is represented by the formula (I)

wherein each of $R^1$, $R^2$, $R^3$ and $R^4$ represents hydrogen, halogen, an alkyl group having 1-4 carbon atoms or an aryl group having 6 ring carbons, and said alcohol is represented by the formula (II)

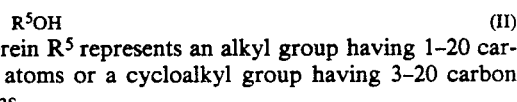

wherein $R^5$ represents an alkyl group having 1-20 carbon atoms or a cycloalkyl group having 3-20 carbon atoms.

3. The process according to claim 2, wherein said conjugated diene is 1,3-butadiene, isoprene, 1,3-hexadiene, 2,4-hexadiene, 2,3-dimethylbutadiene, 2,3-diethylbutadiene, 1,4-diphenylbutadiene, chloroprene, 1,3-heptadiene, 2,4-heptadiene, 1,3-pentadiene, 2-ethyl-1,3-butadiene, 1-phenylbutadiene, 2-chloro-3-methylbutadiene or 1-chlorobutadiene.

4. The process according to claim 2, wherein said alcohol is methanol, ethanol, n-propanol, isopropanol, n-butanol or cyclohexanol.

5. The process according to claim 1, wherein said platinum metal is Pd, Pt, Rh, Ru, Ir or Os.

6. The process according to claim 1, wherein said salt of the platinum metal is a halide, a nitrate, a sulfate, an acetate or a phosphate of Pd, Pt, Rh, Ru, Ir or Os.

7. The proceeds according to claim 1, wherein the metal salt is selected from the group consisting of a copper salt, an iron salt and a manganese salt is a chloride, nitrate, sulfate or acetate.

8. The process according to claim 1, wherein said (c) is an alkali metal compound or an alkaline earth metal compound selected from the group consisting of a carbonate, an acetate, a chloride, a nitrate, a sulfate, a phosphate, an oxalate, an oxide, a hydroxide and a silicate.

9. The process according to claim 1, wherein said (c) is an alkali metal compound or an alkaline earth metal compound selected from the group consisting of a salt of a monocarboxylic acid and a salt of a dicarboxylic acid.

10. The process according to claim 1, wherein said (c) is a rare earth metal compound and is a carbonate, an acetate or an oxide of lanthanum, cerium, yttrium, neodymium, ytterbium, holmium or samarium.

11. The process according to claim 1, wherein said (c) is a metal compound of the groups IIIA, IVA, IVB, VA, VB or VIA and is an oxide or a carbonate of bismuth, lead or indium.

12. The process according to claim 1, wherein said (c) is a metal carbonyl compound selected from the group consisting of $Fe(CO)_5$, $Co(CO)_8$, $Cr(CO)_6$, $Mo(CO)_8$, $W(CO)_8$, $V(CO)_8$, $Ru(CO)_5$, $Rh_4(CO)_{12}$ and $Os(CO)_5$.

13. The process according to claim 1, wherein said (a) is a halide, nitride, sulfate, acetate or phosphate salt of Pd, Pt, Rh, Ru, Ir or Os.

14. The process according to claim 1, wherein said (a) is a nitrile complex and comprises acetonitrile or benzonitrile.

15. The process according to claim 1, wherein said (a) is an amine complex comprising methylamine, butylamine, dimethylamine, dibutylamine, trimethylamine, tributylamine, phenylamine, diphenylamine, triphenylamine or methylphenylamine, or is a phosphine complex comprising methylphosphine, butyulphosphine, dibutylphosphine, tributylphospine, phenylphosphine, diphenylphosphine or triphenylphosphine.

16. The process according to claim 1, wherein said (a) is selected from the group consisting of dichlorotetraamminepalladium, dichlorodiamminepalladium, dichlorobisbenzonitrilephalladium and dichlorobisacetonitrilepalladium.

17. The process according to claim 16, wherein said (b) is selected from the group consisting of cuprous chloride, cupric chloride, ferrous chloride, ferric chloride and manganese chloride.

18. The process according to claim 2, wherein said (a) is in an amount of 0.05 to 20 g atoms as a metal per 100 moles of the conjugate diene; said (b) is in an amount of 0.5 to 50 moles per 1 g atom of said platinum metal or 1 mole of said salt or said complex of said platinum metal; said (c) is an amount of 0.5 to 50 moles per 1 g atom of said platinum metal or 1 mole of said salt or said complex of said platinum metal; and the temperature is 60° to 150° C.

19. The process according to claim 18, wherein said alcohol is selected from the group consisting of methanol, ethanol, n-propanol, isopropanol, n-butanol and cyclohexanol; and said platinum metal is selected from the group consisting of Pd, Pt, Rh, Ru, IR and Os.

* * * * *